(12) United States Patent
Zickman et al.

(10) Patent No.: US 7,059,855 B2
(45) Date of Patent: Jun. 13, 2006

(54) DENTAL IMPLANT SYSTEM (76) Inventors: Albert Zickman, 5455 N. Sheridan Rd., Chicago, IL (US) 60640; Sheldon Lerner, 1636 E. 14th St., Brooklyn, NY (US) 11229

( * ) Notice: Subject to any disclaimer, the term of this patent is extended or adjusted under 35 U.S.C. 154(b) by 191 days.

(21) Appl. No.: 10/382,265

(22) Filed: Mar. 5, 2003

(65) Prior Publication Data

US 2004/0175673 A1 Sep. 9, 2004

(51) Int. Cl.
*A61C 8/00* (2006.01)
*A61C 3/00* (2006.01)

(52) U.S. Cl. .................. 433/174; 433/141
(58) Field of Classification Search ............... 433/173, 433/174, 175, 176
See application file for complete search history.

(56) References Cited

U.S. PATENT DOCUMENTS

| | | | | |
|---|---|---|---|---|
| 3,584,667 A | * | 6/1971 | Reiland | 81/460 |
| 4,459,074 A | * | 7/1984 | Capuano | 411/403 |
| 4,826,434 A | * | 5/1989 | Krueger | 433/174 |
| 4,904,187 A | * | 2/1990 | Zingheim | 433/173 |
| 5,188,800 A | * | 2/1993 | Green et al. | 134/1 |
| 5,601,429 A | * | 2/1997 | Blacklock | 433/174 |
| 5,690,489 A | * | 11/1997 | Carchidi | 433/141 |
| 5,755,574 A | * | 5/1998 | D'Alise | 433/173 |
| 5,871,356 A | * | 2/1999 | Guedj | 433/174 |
| 6,120,292 A | * | 9/2000 | Buser et al. | 433/173 |
| 6,217,331 B1 | * | 4/2001 | Rogers et al. | 433/173 |

* cited by examiner

*Primary Examiner*—Todd E. Manahan
(74) *Attorney, Agent, or Firm*—Bernard Malina; Malina & Associates, P.C.

(57) ABSTRACT

A dental implant system includes a dental implant having an external thread for threading into bone and an internal thread for attachment of a prosthesis. The internal thread has a plurality of notches which accept a complimentary shaped insertion tool. The insertion tool is used to transport the dental implant to the surgical field and to insert the dental implant into the bone.

20 Claims, 8 Drawing Sheets

DENTAL IMPLANT SYSTEM

FIELD OF THE INVENTION

The present invention relates generally to the field of surgical and prosthetic tools and equipment and more particularly, to a dental implant which incorporates a dental implant with a notched cavity.

BACKGROUND OF THE INVENTION

The prior art related to the field of dental implants includes various examples of dental implants and insertion tools.

A typical dental implant according to the prior art includes an external thread which is driven into the bone and an internal thread which accepts an insertion tool. In the past, the insertion tool was screwed into the implant, the implant was screwed into the bone, the insertion tool was unscrewed from the implant and discarded. This process is inherently time consuming and, therefore, disadvantageous.

Another disadvantage of this type of conventional dental insert is related to the process of unscrewing the dental implant from the insertion tool after the implant has been inserted into the bone. The process of unscrewing the insert is disadvantageous because the process inherently tends to loosen the contact between the insert and the bone.

Another example of prior art dental inserts is shown in U.S. Pat. No. 4,960,381 issued to Gerald A. Niznick for a Screw-Type Dental Implant Anchor. The Niznick patent shows a screw-type dental implant anchor which includes an externally threaded body portion which includes an internal structure for engaging an insertion tool. The top portion of the implant anchor is open and in registry with an internally-threaded portion. The top portion of the anchor forms a head portion which includes a hex-shaped cavity in its inner wall surfaces for receiving a hex wrench. The internal hex-shaped configuration is intended to allow the insertion of the anchor in the jawbone of a patient using an Allen-type wrench.

One of the significant disadvantages of the Niznick device is related to the arrangement of the hex-shaped cavity which is positioned directly above the internally threaded portion. As shown and described in the Niznick patent, the smaller distance across the hex-shaped cavity is greater than the external diameter of the internal threads. This configuration creates stress concentrations which results in high stress lines along the hex corners. This problem has resulted in numerous implant fractures.

Another example of prior art dental inserts is shown in U.S. Pat. No. 6,464,500 to Don D. Popovic for a Dental Implant and Abutment System. The Popovic patent showed a screw-type dental implant anchor which includes an externally threaded body portion which includes an internal structure for engaging an insertion tool. The top portion of the implant anchor includes an internally threaded portion. A hex-shaped cavity is located below the internally threaded portion for the purpose of receiving a hex wrench. As in the Niznick patent previously described, the hex-shaped cavity is intended to facilitate the insertion of the anchor in the jawbone of a patient using an Allen-type wrench. As a result of the location of the hex-shaped cavity below the internally threaded portion, the distance between corners of the hex-shaped cavity is smaller than the internally threaded portion.

The hex-shaped cavity is therefore so small that at normal insertion torques, there is the distinct possibility of damage to the insertion tool and damage to the insert. This is especially true in the event that the insert binds prematurely in hard bone. This is caused by the required relationship between the internal threads and the hex-shaped cavity. The largest thread normally used has a diameter of about 1.5 millimeters, mm. The distance between the corners of the hex has to be smaller than 1.5 mm, otherwise the insertion tool would not clear the internal threads.

As a result, neither the configuration of the Niznick device with the hex-shaped cavity above the internally threaded portion nor the Popovic configuration with the hex-shaped cavity below the internally threaded portion provides a satisfactory dental implant.

Another example of a prior art dental implant is shown in U.S. Design Pat. No. D446,859 issued to Steven M. Hurson for a Multi-Lobed Dental Implant. The Hurson patent shows a screw-type dental implant which includes an externally threaded body portion and an internal cavity for engaging an insertion tool. The Hurson device is generally similar to the Niznick device and the top portion of the implant is open and in registry with an internally threaded portion. The top portion of the implant includes a multi-lobed cavity. In a manner similar to the Niznick device, the multi-lobed cavity extends beyond the external or maximum diameter of the internal threads. As explained in connection with the Niznick device, this configuration creates stress-concentrations where there are discontinuities in the cross-section, such as at the corners of the lobes. As explained previously, these stress concentrations can lead to loss of structural integrity of the implant. These problems are increased when there is an attempt to manufacture the Hurson or the Niznick devices in the relatively narrow configurations which are required for narrow edentulous areas.

An example of the problems associated with prior art implants is described in an article titled "Ridge Augmentation for Immediate Postextractive Implants: Eight Year Retrospective Study" by A. Ashman, DDS, J. Lo Pinto, DDS, and J. Rosenlicht, DMD, in *Practical Periodontics and Aesthetic Dentistry*, Vol. 7, No. 2, March 1995, page 89. The article shows an insert with a hex-shaped cavity cut in the internal thread, in which the internal thread was stripped by the insertion tool during surgical placement. This problem resulted in a need to cut a new thread into the implant.

Despite the developments of the prior art, there remains a need for a dental implant which can be installed in a safe and reliable manner.

OBJECTS AND SUMMARY OF THE INVENTION

It is an object of the present invention to provide a dental implant system which includes a dental implant having a notched cavity and a complimentary shaped insertion tool.

Another object of the present invention is to provide a dental implant system which includes a threaded cavity which can accept either a threaded fastener or a multilobed insertion tool.

Another object of the present invention is to provide a dental implant system which can be manufactured in relatively narrow configurations and which can be placed in very narrow edentulous areas.

Another object of the present invention to provide a dental implant which can accept an insertion tool with a friction fit.

Another object of the present invention is to provide a dental implant which does not require a screw-type of connection with the insertion tool.

Another object of the present invention is to provide a dental implant which can be quickly installed on an insertion tool.

Another object of the present invention is to provide a dental implant which demonstrates relatively great resistance to fracture thereby providing a safe and reliable installation.

Another object of the present invention is to provide a dental implant which can be quickly and easily removed from an insertion tool after the dental implant is inserted into the bone.

Another object of the present invention is to provide a dental implant which does not require being unscrewed from the insertion tool after the dental implant has been inserted into the bone.

Yet another object of the present invention is to provide a dental implant which facilitates secure transportation from the dental implant pack to the surgical field.

Other objects and advantages of the invention will become evident hereinafter.

In accordance with the present invention, there is provided a dental implant system which incorporates a dental implant which includes an external thread for threading into the bone. The implant includes an internally threaded portion which accepts a post for the attachment of a prosthesis. A key feature of the invention is a notched cavity which is cut through the internally threaded portion. The notched cavity preferably has a configuration in the shape of a circular array with six grooves with the external diameter of the grooves approximately equal to the major diameter of the threads and the internal diameter of the grooves approximately equal to the minor diameter of the threads. In addition, the dental insert includes an internally tapered portion. The internally tapered portion and the notched cavity accept an insertion tool of complementary shape.

The insertion tool can be inserted into the dental implant and then used to transport the dental implant to the surgical field in a safe and convenient manner. The insertion tool can then be used to insert the dental implant into the bone. After the insertion process has been completed, the insertion tool is simply withdrawn from the implant without a need for unscrewing or other cumbersome techniques.

BRIEF DESCRIPTION OF THE DRAWINGS

Other important objects and advantages of the invention will be apparent from the following detailed description of the invention taken in connection with the accompanying drawings in which.

DETAILED DESCRIPTION OF THE INVENTION

With reference to the drawings, in which like reference numbers designate like or corresponding parts throughout, there is shown in FIGS. 1–12 a dental implant system 10 made in accordance with the present invention, which includes a dental implant 12 which has a body portion which has a self-tapping threaded exterior surface 16. The end 18 of the body portion 14 has a full radius resulting in a convex configuration. The dental implant system 10 also includes an insertion tool 20 which will be described presently.

The following dimensions are by way of example only and are not to be considered as limitations on the present invention. The overall length of the dental implant 12 is generally between 5 mm and 20 mm. The outside diameter of the dental implant 12 is generally between 3 mm and 7 mm. The threaded exterior surface 16 is used to anchor the dental implant 12 into the patient's bone. The dental implant 12 includes an internally threaded portion 21. The function of the internal thread 22 is to facilitate attachment of a cover screw and prosthetic components or an abutment 24. The internal thread 22 typically has a major diameter which ranges between 1.3 mm and 2.0 mm.

The upper portion 26 of the body portion 14 is unthreaded and is outwardly flared. The radius of curvature of the surface 28 of the outwardly flared portion 26 as shown by the radius "R" in FIG. 3. has a preferred radius in the order of approximately 0.5 inches. The end 30 of the body portion 14 has an inwardly tapered cavity 32 which leads from the end 30 of the body portion 14 to an internally threaded portion 22 which extends inwardly from a plane 34 at the base 36 of the tapered cavity 32.

The end 30 of the body portion 14 has a chamfered portion 38 which has a preferred angle in the order of 45 degrees.

Figure 1:
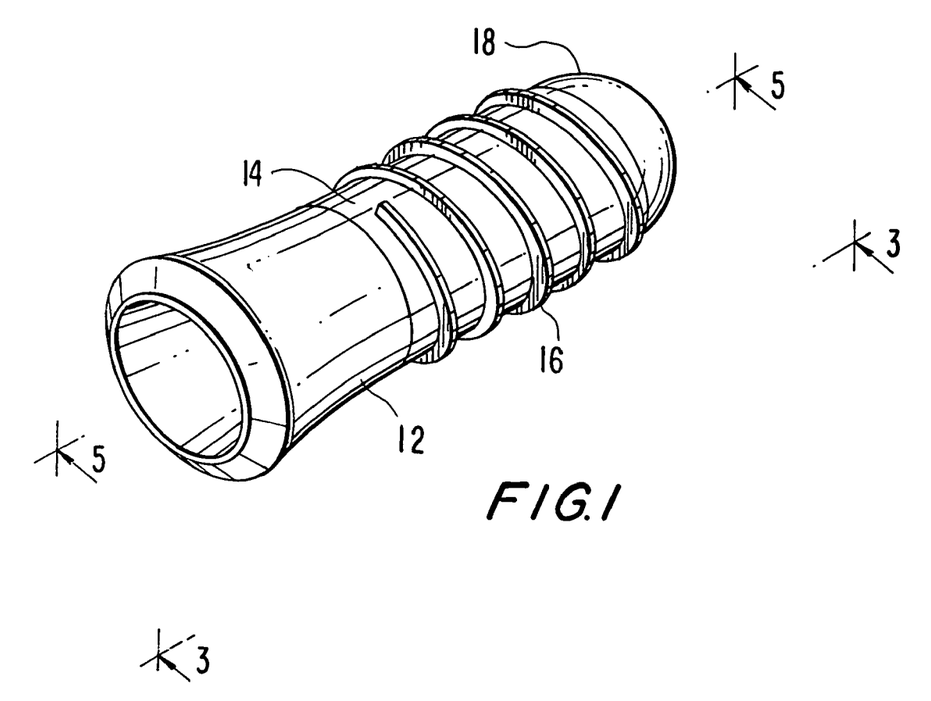
FIG. 1 is an overall perspective view of a dental implant made according to the present invention.
Figure 2:
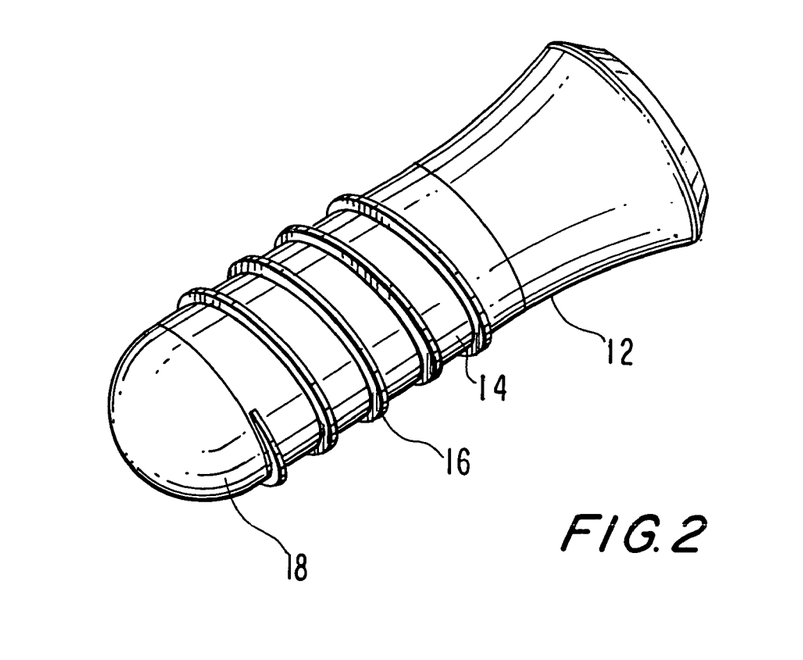
FIG. 2 is another overall perspective view of the dental implant of FIG. 1.
Figure 3:
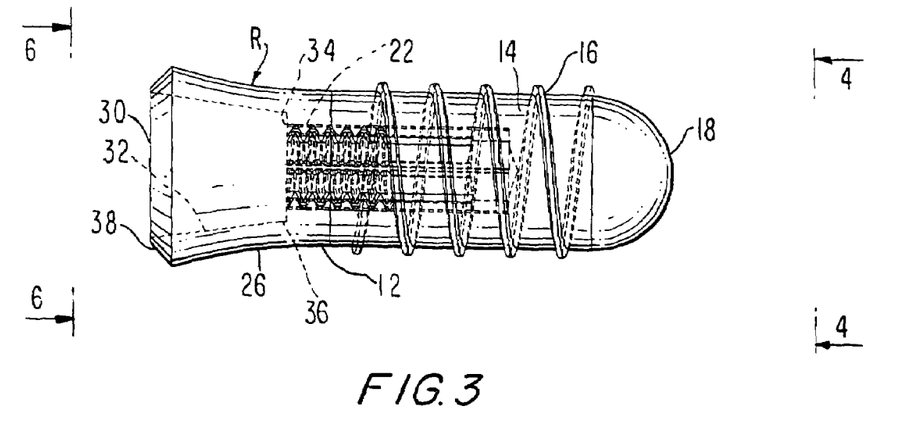
FIG. 3 is a side elevation view taken along the line 3—3 of FIG. 1.
Figure 4:
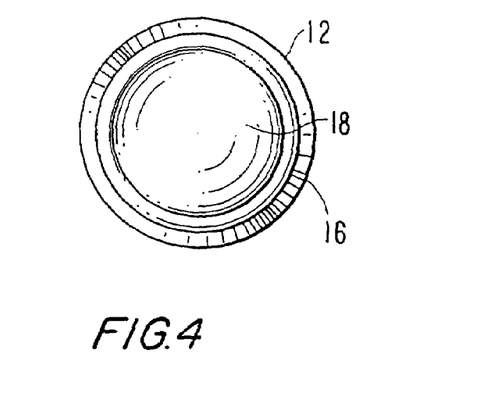
FIG. 4 is an end view along the line 4—4 of FIG. 3.
Figure 5:
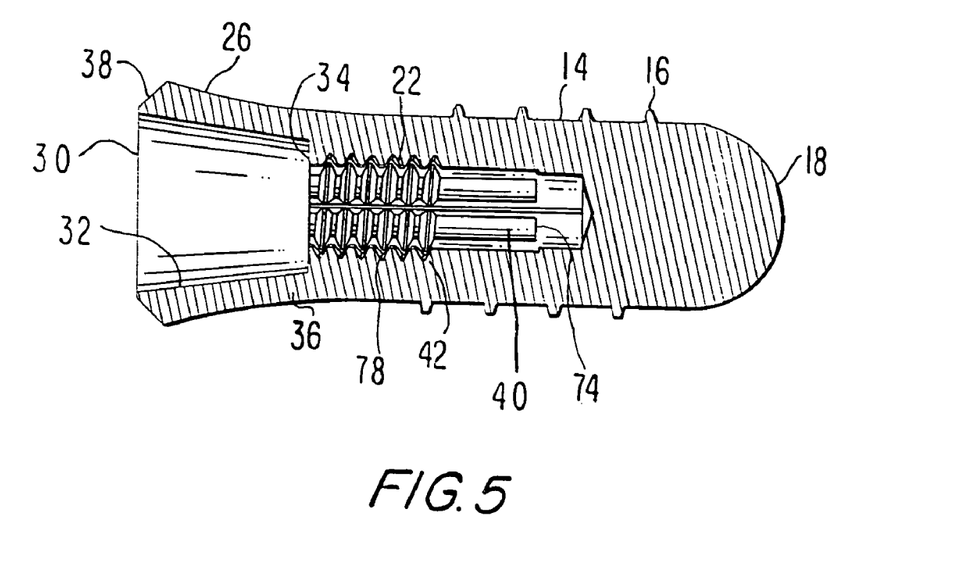
FIG. 5 is a cross-sectional view taken along the line 5—5 of FIG. 1.
Figure 6:
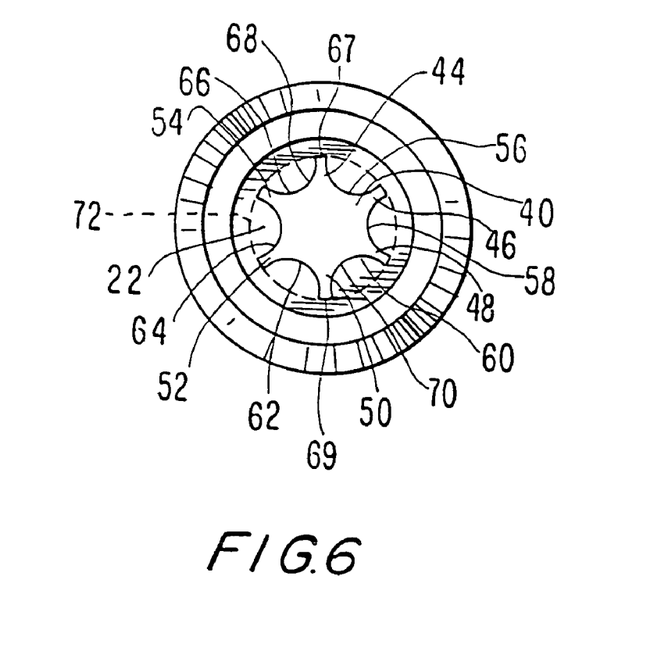
FIG. 6 is an end view taken along the line 6—6 of FIG. 3.

A notched or grooved cavity 40 which is a key feature of the present invention, extends inwardly from the plane 34 at the base 36 of the tapered cavity 32. As is best shown in FIGS. 3–6, the grooved cavity 40 extends past the end 42 of the internally threaded portion 22. The grooved cavity 40 as shown in FIG. 6 has six grooves 44, 46, 48, 50, 52, 54 with the depth of the grooves extending to a point approximately equal to the major diameter of the threaded portion 22 and with the minor diameter of the groove array approximately equal to the minor diameter of the threaded portion 22. Wall portions 56, 58, 60, 62, 64, 66 defining the grooves are generally curved.

The curved wall portions 56, 58, 60, 62, 64, 66 form an important advantage of the present invention 10. Prior art cavities used for transmitting torque have generally utilized a hexagonal shape. In a hexagon, the distances between the opposing flat portions of a hexagon are nearly equal to the distances between the opposing corner portions of the hexagon. There is thus a relatively small ratio between the dimensions between the corners of the hexagon and the flat portions of the hexagon.

The relatively small ratio between the dimensions between the corners of a hexagon and the flat portions of a hexagon results in a tendency to strip or fail especially when a hexagonal cavity is formed in the relatively small sizes required for dental inserts.

In the grooved or notched cavity 40, according to the present invention, which is formed by the concave curved wall portions 56, 58, 60, 62, 64, 66, there is a relatively large ratio between the larger dimension as measured between the corners of the grooves typically indicted by the numerals 67, 69 and the relatively smaller dimension as measured between the closest points of the curved wall portions typically indicated by the numerals 68, 70. The reference numerals 68, 70 thus indicate the narrowest portion of the grooved cavity 40. This relatively large ratio enables the cavity 40 to be cut into the threads 22 without the danger of weakening the threads.

As indicated above in FIG. 6, the grooves or notches 44, 46, 48, 50, 52, 54 are formed to a depth which approximates the major diameter of the internal thread 22 as indicated by the broken lines 72.

As shown in FIGS. 3–6, the end 74 of the grooved cavity 40 extends past the inner end 42 of the internally threaded portion 22. Alternatively, the end 74 of the grooved cavity 40 may end at the inner end 42 of the threaded portion 22. In another alternative embodiment, the end 74 of the grooved cavity 40 may end at an intermediate portion of the threaded portion 22 as denoted by the reference numeral 78 in FIG. 5.

Figure 11:
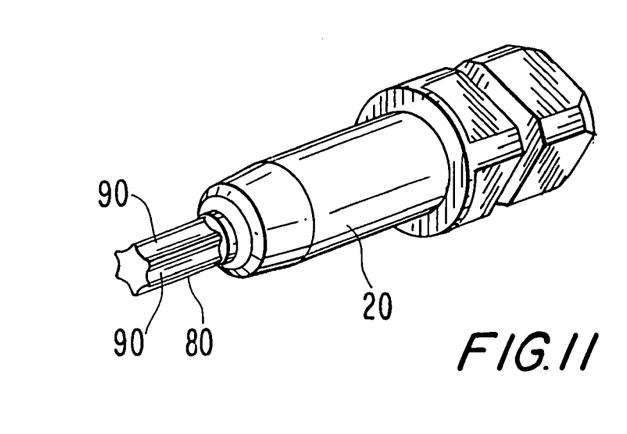
FIG. 11 shows an overall perspective view of an insertion tool for use with the dental implant of FIG. 1.
Figure 12:
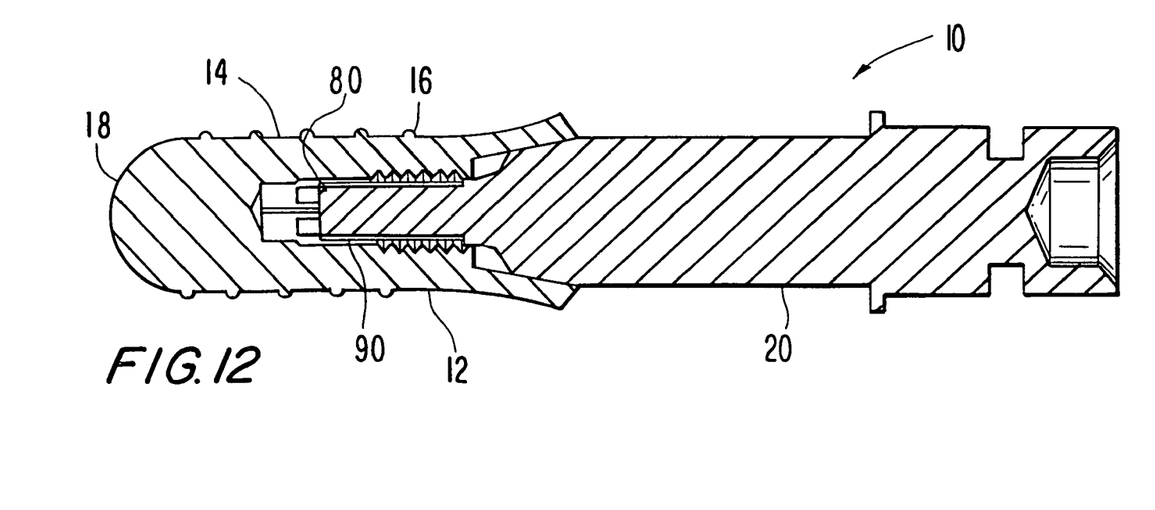
FIG. 12 is a cross-sectional view showing the insertion tool of FIG. 11 inserted into the dental implant of FIG. 1.

As is shown in FIGS. 3–6, the internally notched or grooved cavity 40 is cut through the internally threaded portion 22 and can easily accept the grooved portion 80 of the installation tool 20 which is shown in FIGS. 11 and 12. The grooved portion 80 of the installation tool 20 compliments the grooved cavity 40 of the dental implant 10. The insertion tool 20 is typically made of instrument grade stainless steel.

Figure 7:
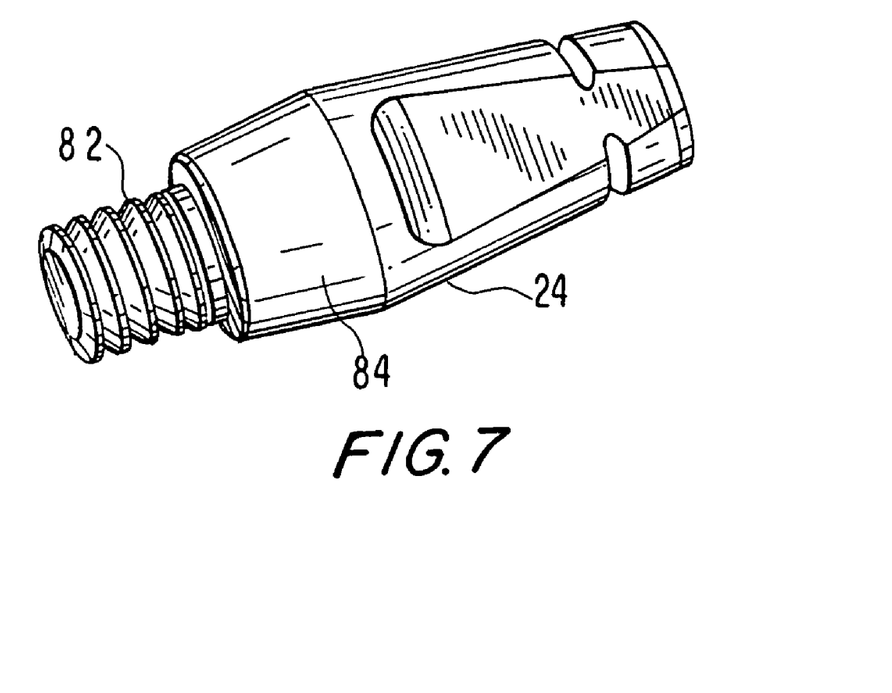
FIG. 7 is an overall perspective view of an abutment for use with the dental implant of FIG. 1.
Figure 8:
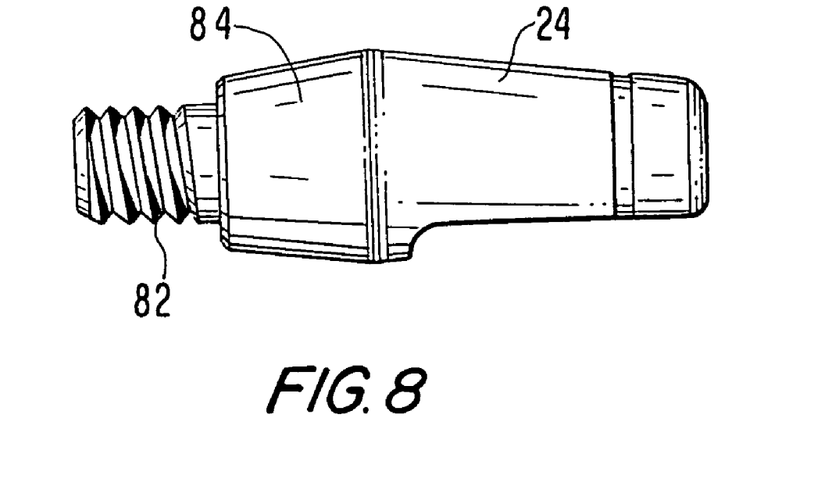
FIG. 8 is a side elevation view of the abutment of FIG. 7.
Figure 9:
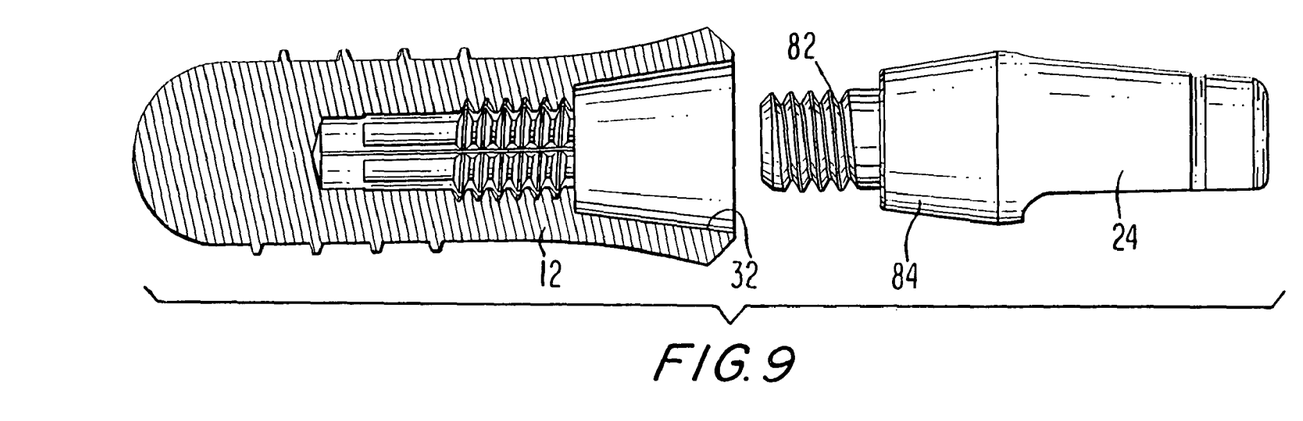
FIG. 9 shows the start of the insertion of the abutment of FIG. 8 into the dental implant of FIG. 1.
Figure 10:
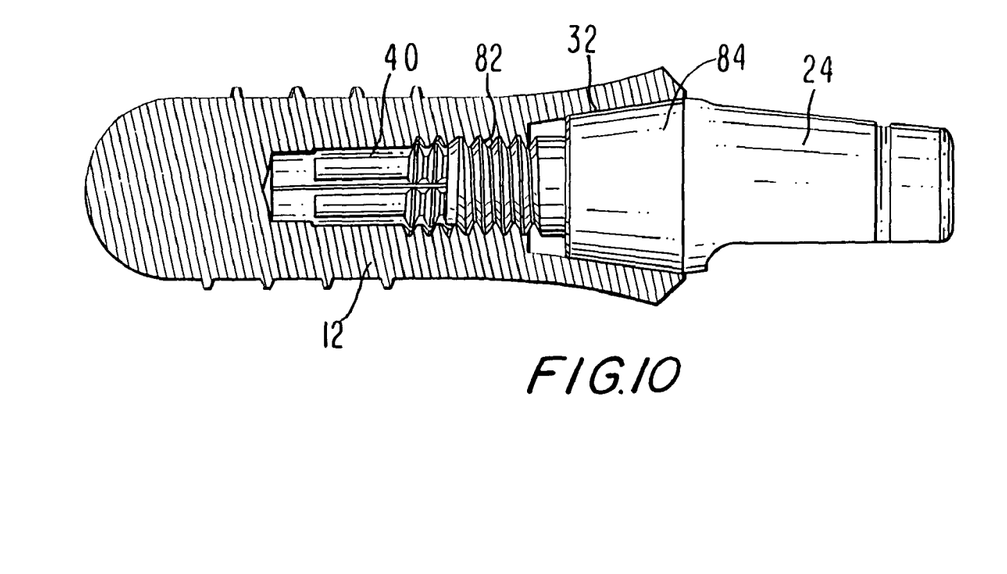
FIG. 10 shows the abutment inserted into the dental implant.

After the dental implant 12 has been inserted into the patient's bone using the installation tool 20, the installation tool 20 is withdrawn. A screw type of abutment 24 which is shown in FIGS. 7 and 8 is installed into the dental implant 12 as is shown in FIGS. 9 and 10. The threaded portion 82 of the abutment 24 engages the internal thread 22. As is best shown in FIG. 10, the tapered cavity 32 of the dental implant 10 compliments the tapered portion 84 of the abutment 82 resulting in a secure fit. The outwardly flared portion 26 of the dental implant 12 and the chamfered portion 38 cooperate with the abutment 82 to provide an efficient transfer of the dental forces with a minimum size and weight structure.

One of the key advantages of the dental implant 12 of the present invention is related to the relatively great strength of the dental implant 12 as compared with prior art devices. Torque testing of the dental implant 12 of the present invention and the hex cavity device shown in the Popovic patent U.S. Pat. No. 6,464,500 is summarized in Table 1.

TABLE 1

COMPARATIVE RESISTENCE TO TORQUE

| UNIT | APPLIED TORQUE (Newton Centimeters) | RESULTS |
| --- | --- | --- |
| Prior art Hex-cavity device Popovic Patent U.S. Pat. 6,464,500 | 100 | Fracture of the insertion tool |
| Dental Implant according to the present invention | 150–200 | No fracture or weakening |

Typical insertion torque is usually 50–130 Ncm. However, this torque can reach higher values if the implant binds prematurely in hard bone.

The significantly increased resistance to torque experienced during the installation into the bone of a patent by the dental implant 12 according to the present invention results in a significant increase in the safety and reliability of the installation process.

The dental implant 12 may be made of any implantable metal or ceramic material including commercially pure titanium.

A preferred material for the dental implant 12 according to the present invention has been found to be 6AL-4V-EL1 titanium.

Figure 13:
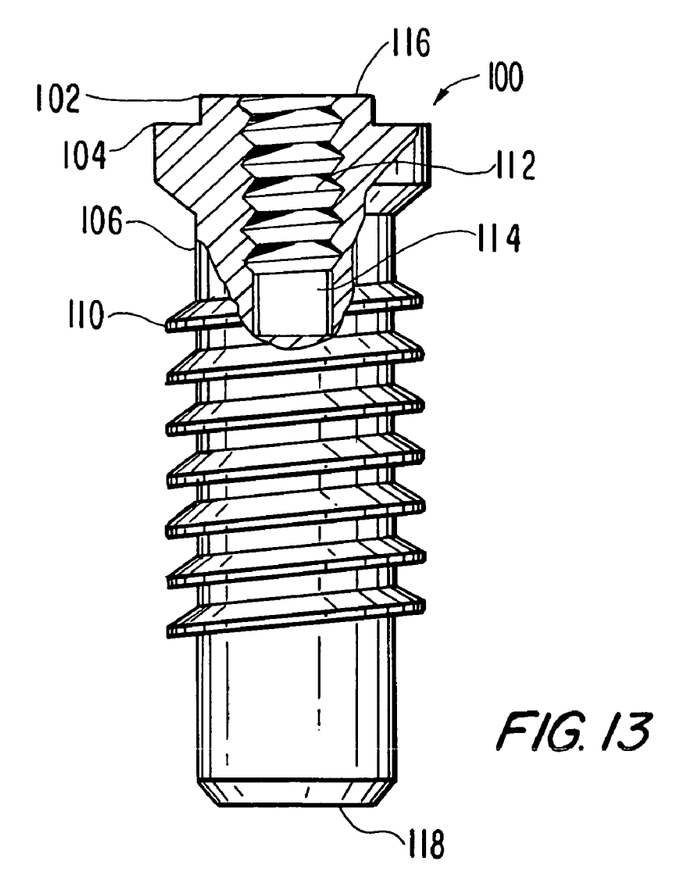
FIG. 13 is a side view partially in section showing an alternative embodiment of the dental implant of FIG. 1.
Figure 14:
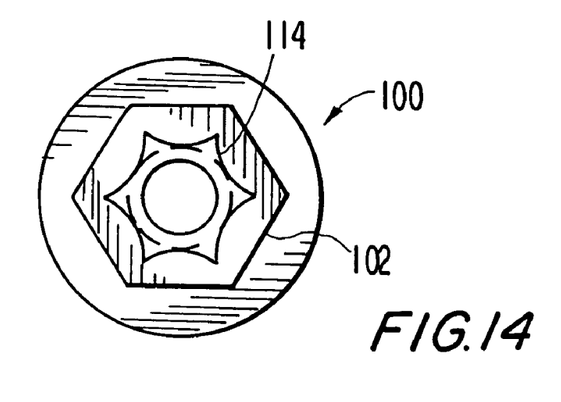
FIG. 14 is an end view of the dental implant of FIG. 13.

FIGS. 13–14 show an alternate embodiment 100 of the present invention which incorporates an external hex surface 102 at the upper end 104 of the implant. The body 106 of the implant 100 includes an outside surface 108 with a thread pattern 110 for anchoring the implant 100 into bone and an internal thread 112 which is similar to the internal thread 22 previously described. In the embodiment 100 shown in FIGS. 13–14, the tapered portion 32 previously described has been eliminated and the grooved cavity 114, which is similar to the grooved cavity 40 previously described, extends to the top surface 116 of the implant 100. The end 118 of the implant 100 is flat.

Figure 15:
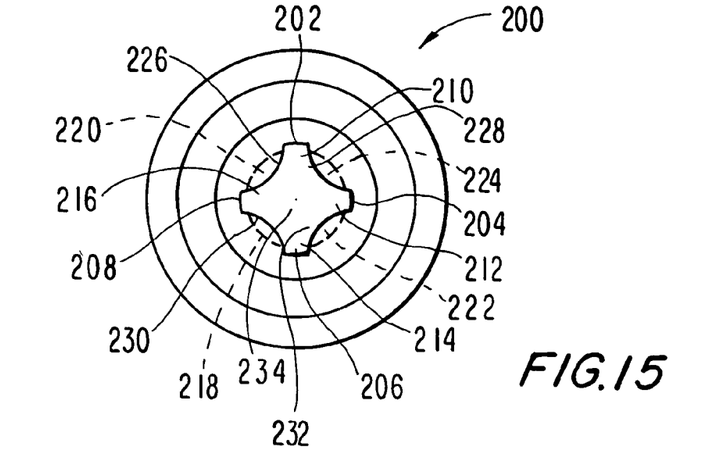
FIG. 15 is an end view generally similar to FIG. 6 showing another embodiment of the dental implant of FIG. 1.

In the alternative embodiment of the invention 200 shown in FIG. 15, the ends 202, 204, 206, 208 of the grooves 210, 212, 214, 216 extend beyond the major diameter of the internal thread 224 which is shown in broken lines 218. Alternatively, the grooves 210, 212, 214, 216 may extend to points 230, 232 indicated in FIG. 15 which define a diameter which is smaller than the major diameter 218 of the internal thread 224. As described previously, the grooves 210, 212, 214, 216 are, in part, defined by curved portions 226, 228, 230, 232.

Figure 16:
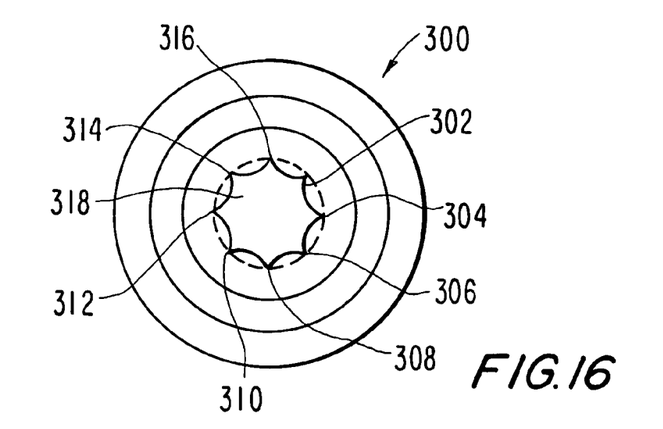
FIG. 16 is an end view generally similar to FIG. 6 showing yet another embodiment of the dental implant of FIG. 1.

The alternative embodiment of the invention 200 shown in FIG. 15 has four (4) grooves 210, 212, 214, 216 or notches, while the alternative embodiment 300 shown in FIG. 16 has eight (8) grooves 302, 304, 306, 308, 310, 312, 314, 316 or notches. The number of grooves or notches may have a preferred range between two (2) and eight (8).

The construction of the grooves 302, 304, 306, 308, 310, 312, 314, 316 is generally similar to the construction of the grooves previously described in connection with FIGS. 6 and 15. With the exception of the grooved cavities 234, 318, the overall construction of the embodiments 200 and 300 shown in FIGS. 15 and 16 is generally similar to the construction of the insert 12 shown in FIGS. 1–6. The ends 202, 204, 206, 208 of each of the grooves 210, 212, 214, 216 in FIG. 15 are shown as convexly curved. This construction is typical of each of the grooves in the embodiments 12, 100, 288, 300 shown in FIGS. 1–6, 13, and 16.

Figure 17:
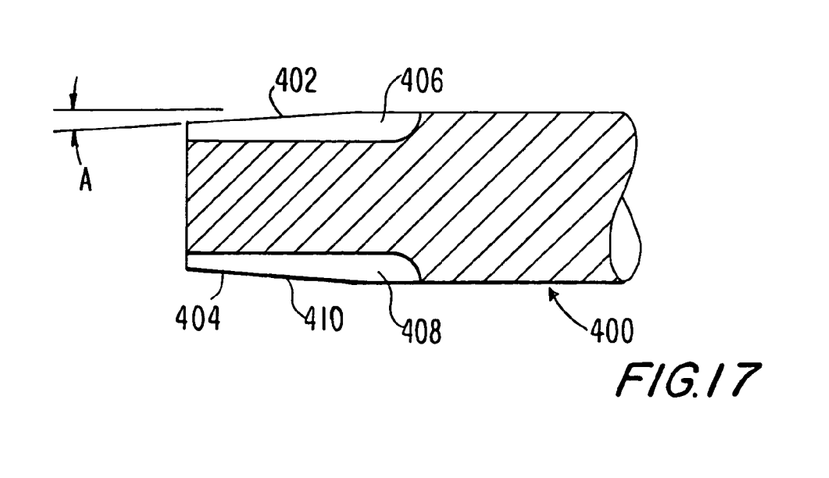
FIG. 17 is a cross-sectional view of an alternative embodiment of the insertion tool shown in FIG. 11.

In the insertion tool 20 shown in FIGS. 11 and 12, the grooves 90 are generally parallel to a central axis. In the alternative embodiment of the insertion tool 400 shown in FIG. 17, the walls 404, 402, which define the grooves 406, 408, each include a tapered portion 410 which facilitates a friction fit with the dental inserts 12, 100, 200, 300. The tapered portion 410 is defined in part by an angular portion designated by the angle "A" in FIG. 7.

The foregoing specific embodiments of the present invention as set forth in the specification herein are for illustrative purposes only. Various deviations and modifications may be made within the spirit and scope of the invention without departing from the main theme thereof.

What is claimed is:

1. A dental implant system comprising:
   a dental implant and an insertion tool, with said dental implant comprising
   an implant body having an outer surface, a first end and a second end;
   an externally threaded portion formed on said outer surface of said implant body;
   an internally threaded portion accessible from said first end of said implant body;
   a plurality of notch portions formed in said internally threaded portion and with said insertion tool comprising an insertion tool body having an end;
   a driving portion disposed on said end of said insertion tool body, with said driving tool portion comprising,
   a plurality of projecting portions proportioned to complement said plurality of notch portions formed in said internally threaded portion thereby enabling said insertion tool to engage said implant body and form a driving connection with said implant body further comprising a tapered cavity formed in said dental implant and disposed leading from said first end of said implant body to said internally threaded portion, said tapered cavity frictionally engaging said insertion tool.

2. The dental implant system as claimed in claim 1 wherein each of said plurality of notch portions comprises a pair of curved wall portions.

3. The dental implant system as claimed in claim 2 wherein said curved wall portions comprise concave wall portions.

4. The dental implant system as claimed in claim 1 wherein said dental implant has a longitudinal dimension wherein said internally threaded portion extends longitudinally relative to said dental implant and wherein said notch portions each comprise a groove formed longitudinally relative to said dental implant.

5. The dental implant as claimed in claim 1 wherein said externally threaded portion comprises a self-tapping externally threaded portion.

6. The dental implant as claimed in claim 1 wherein said internally threaded portion has a major diameter and a minor diameter and wherein each of said notch portions extend to a point generally equal to said major diameter of said threaded portion.

7. The dental implant as claimed in claim 1 wherein said internally threaded portion has a major diameter and a minor diameter and wherein each of said notch portions extends to an intermediate point between said minor diameter and said major diameter.

8. The dental implant as claimed in claim 1 wherein said internally threaded portion has a major diameter and a minor diameter and wherein each of said notch portions extends to a point at a diameter greater than said major diameter.

9. The dental implant as claimed in claim 1 wherein said internally threaded portion has a first end disposed proximately to said first end of said implant body and a second end disposed distally relative to said first end of said implant body and wherein said second end of said internally threaded portion extends to a point generally in line with an intermediate portion of said externally threaded portion.

10. The dental implant as claimed in claim 1 wherein said internally threaded portion has a first end disposed proximately to said first end of said implant body and a second end disposed distally relative to said first end of said implant body and wherein said externally threaded portion has a first end and disposed proximately to said first end of said implant body and wherein said second end of said internally threaded portion extends to a point beyond said first end of said externally threaded portion.

11. The dental implant as claimed in claim 1 wherein said internally threaded portion has a first end disposed proximately to said first end of said implant body and a second end disposed distally relative to said first end of said implant body and said externally threaded portion has a first end and a second end, and wherein said second end of said internally threaded portion extends to a point intermediate between said first and said second ends of said externally threaded portion.

12. The dental implant as claimed in claim 1 wherein said first end of said dental implant body further comprises an outwardly flared portion.

13. The dental implant as claimed in claim 12 wherein said outwardly flared portion comprises a curved portion.

14. The dental implant as claimed in claim 1 wherein said first end of said dental implant body comprises a chamfered portion.

15. The dental implant as claimed in claim 1 wherein said second end of said implant body comprises a rounded portion.

16. The dental implant system as claimed in claim 1 wherein said second end of said implant body comprises a flat portion.

17. The dental implant as claimed in claim 1 wherein the quantity of notches formed in said internally threaded portion has a preferred minimum value of three notches and a preferred maximum value of eight notches.

18. The dental implant system as claimed in claim 1 wherein said insertion tool has a longitudinal axis and wherein said projecting portions are generally parallel to said longitudinal axis.

19. The dental implant system as claimed in claim 1 wherein said insertion tool has a longitudinal axis and wherein said projecting portions are tapered relative to said longitudinal axis.

20. The dental implant system as claimed in claim 1 wherein the quantity of notches formed in said internally threaded portion is at least two.

* * * * *